United States Patent [19]

Fellmann et al.

[11] Patent Number: 5,017,735
[45] Date of Patent: May 21, 1991

[54] SELECTIVE SORPTION OF 2,6-DIISOPROPYLNAPHTHALENE

[75] Inventors: Jere Fellmann, Livermore; Paul R. Wentrcek, Redwood City; Peter Kilner, Sunnyvale, all of Calif.

[73] Assignee: Catalytica, Inc., Mountain View, Calif.

[21] Appl. No.: 384,647

[22] Filed: Jul. 24, 1989

[51] Int. Cl.$^5$ ................................................. C07C 7/13
[52] U.S. Cl. ..................................... 585/820; 585/826; 585/827; 585/828; 208/310 Z
[58] Field of Search .................... 208/310 Z; 585/820, 585/826, 827, 828

[56] References Cited

U.S. PATENT DOCUMENTS

| | | | |
|---|---|---|---|
| 3,310,486 | 3/1967 | Broughton et al. | 208/310 Z |
| 3,668,267 | 6/1972 | Hedge | 208/310 Z |
| 4,698,453 | 10/1987 | Miwa et al. | 585/820 |
| 4,791,235 | 12/1988 | Maki et al. | 585/828 X |

FOREIGN PATENT DOCUMENTS 1199921 8/1989 Japan.
2199590A 7/1988 United Kingdom.

OTHER PUBLICATIONS

Bulk Separations Via Adsorption, D. B. Broughton, CEP Magazine, (Oct., 1977), pp. 49–51.
Meier, *Atlas of Zeolite Structure Types*, Second Revised Edition, 1987, pp. 62–63.

Primary Examiner—Curtis R. Davis
Assistant Examiner—William Diemler
Attorney, Agent, or Firm—E. Thomas Wheelock

[57] ABSTRACT

A process for enriching the fraction of 2,6-diisopropylnaphthalene contained in a quantity of mixed dialkylated naphthalenes. The mixed dialkylated naphthalenes are contacted with an adsorbant bed containing one or more molecular sieves which demonstrate shape selective preference for the 2,6-diisopropylnaphthalene isomer over other dialkylated naphthalenes. The adsorbant bed is then contacted with a desorbant capable of desorbing the 2,6-diisopropylnaphthalene from the pores of the adsorbant.

31 Claims, 1 Drawing Sheet

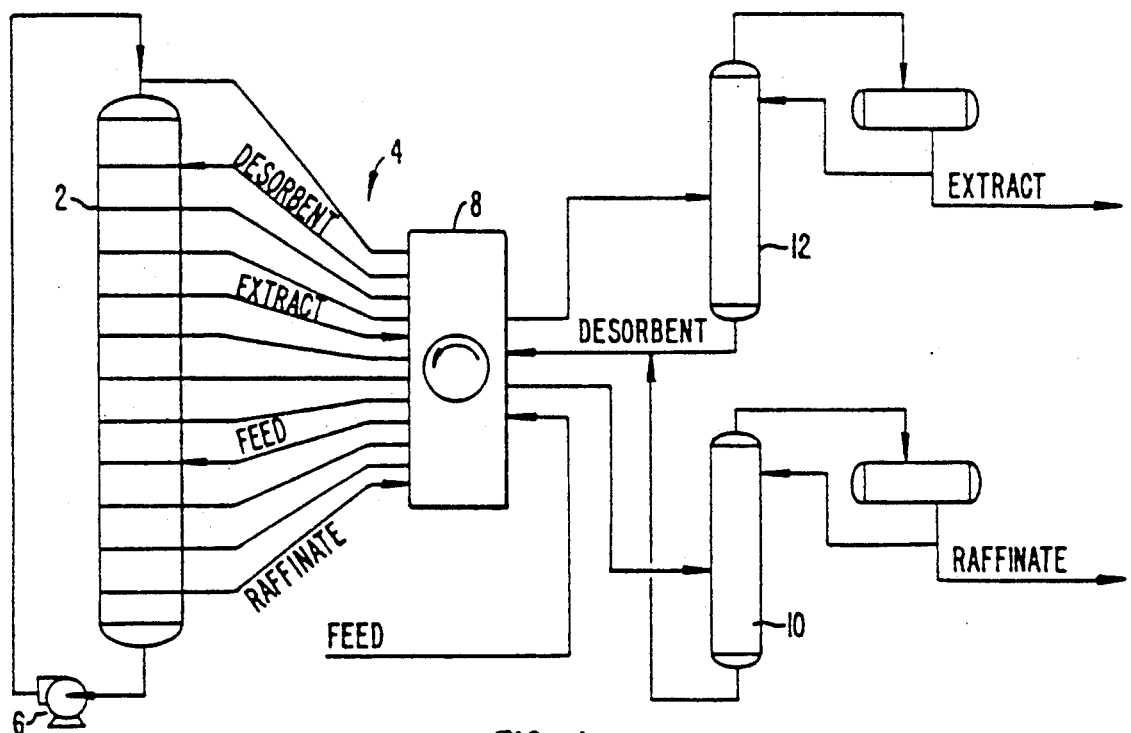
FIG._1.
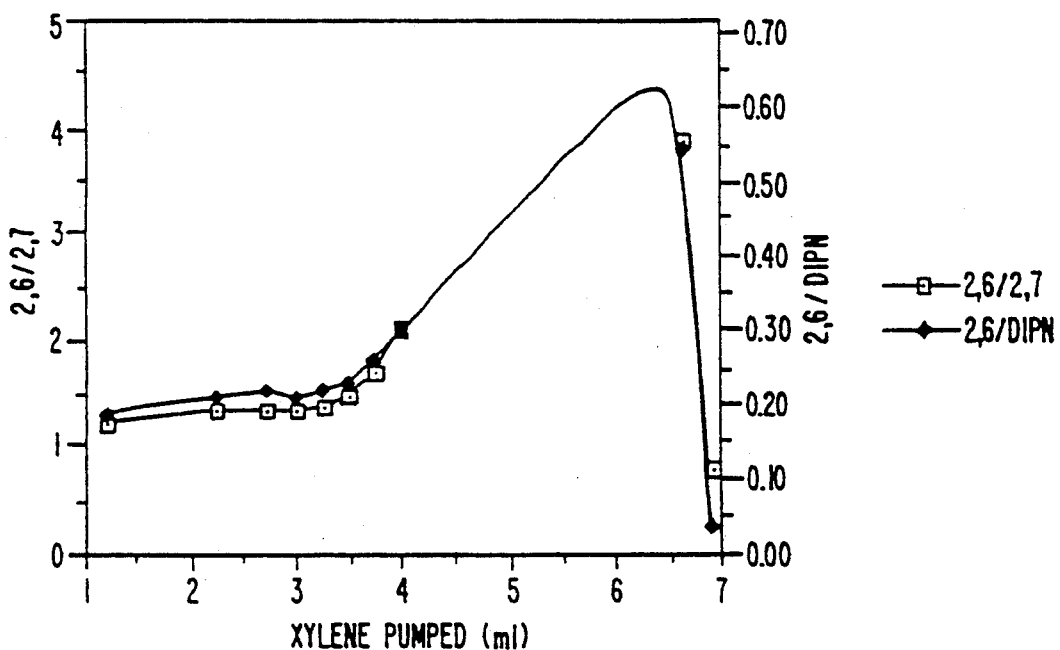
FIG._2.

SELECTIVE SORPTION OF 2,6-DIISOPROPYLNAPHTHALENE

TECHNICAL FIELD OF INVENTION

The invention relates to a process for the separation of the 2,6-diisopropylnaphthalene isomer from a feed stream of mixed isopropylnaphthalenes. A shape-selective adsorbant is employed resulting in a process that is more efficient than processes based upon prior separation techniques.

BACKGROUND OF THE INVENTION

The present invention relates to a process for separating 2,6-diisopropylnaphthalene from other isopropylnaphthalene isomers. The 2,6-diisopropyl isomer of naphthalene is of keen interest for the production of certain disubstituted aromatics which, in turn, are employed in the synthesis of liquid crystal polymers and specialty polyesters.

Such liquid crystal polymers and specialty polyesters would appear commercially attractive if either 2,6-dihydroxynaphthalene or 2,6-dicarboxynaphthalene were readily available. Unfortunately, these materials are not commercially produced because cheap, feed stocks do not exist. A viable feed stock which is convertible into either the dihydroxy or dicarboxy monomers, based upon known technology, is 2,6-diisopropylnaphthalene.

In any manufacture of diisopropylnaphthalene, it is clear that some monoisopropyl- and triisopropyl-products and a mix of diisopropyl isomers will also be obtained. In any crude diisopropylnaphthalene product which is not particularly enriched in the 2,6-diisopropylnaphthalene isomer, isomer separation by thermal distillation is very inefficient and difficult because the boiling points of 2,6-diisopropylnaphthalene and 2,7-diisopropylnaphthalene are very close. Similarly, 2,6-diisopropylnaphthalene separation by fractional crystallization using melting points is inefficient and suffers from yield problems because of the loss of the desired product in the mother liquor, and because of large recycled streams.

It is taught in U.K. patent application No. 2,199,590, filed on Nov. 27, 1987, that a specific isomer of dimethylnaphthalene can be separated from other isomers when a zeolite Y containing specific metallic ions is used as an adsorbant in combination with a specific desorbant. However, the adsorbant taught for use in the separation of the particular dimethylnaphthalene of the British reference would be of little value in isolating 2,6-diisopropylnaphthalene from other diisopropylnaphthalene isomers, since diisopropylnaphthalenes are larger molecules than dimethylnaphthalenes.

It is thus an object of the present invention to provide a selective adsorbant which has proven to be efficient in the selective adsorption of 2,6-diisopropylnaphthalene from a mixture of diisopropylnaphthalene compounds.

It is a further object of the invention to provide a process for enriching the fraction of 2,6-diisopropylnaphthalene contained in a feed stream of mixed dialkylated naphthalenes without engaging costly and inefficient distillation and crystallization techniques of the prior art.

It is still a further object of the present invention to provide a process for recovering substantially pure 2,6-diisopropylnaphthalene from a mixture of diisopropylnaphthalene isomers using selective adsorption in combination with conventional separation techniques such as fractional crystallization or distillation.

These and further objects will be more fully appreciated when considering the following disclosure and appended drawings wherein:

FIG. 1 represents a simulated moving bed column which can be employed in practicing the present invention; and FIG. 2 is a graph demonstrating the efficacy of the present invention in illustrating ratios of 2,6-diisopropylnaphthalene adsorbed with the volume of desorbant employed.

SUMMARY OF THE INVENTION

The present invention is both to a shape selective adsorbant for the selective adsorption of 2,6-diisopropylnaphthalene from a feed stream of mixed diisopropylnaphthalenes as well as to a process for separating the 2,6-diisopropyl isomer from a mixture of isomers of diisopropylnaphthalenes. It was discovered that the optimum shape selective adsorbant is a class of crystalline molecular sieves all of which are characterized as having 12 member oxygen rings and pore aperture dimensions between approximately 5.5Å and 7.0Å. The process involves contacting a quantity of mixed diisopropylnaphthalene isomers with an adsorbant bed containing one or more of the above crystalline molecular sieves.

Following the adsorption step, the material held up in the interstices is removed. At this point, the bed contains sorbed material that is rich in 2,6-diisopropylnaphthylene. The material sorbed by the bed is then displaced from the bed with a suitable desorbant. The desorbant can then be separated from the desorbed diisopropylnaphthalenes and recycled. The product is a material rich in 2,6-diisopropylnaphthalene. If desired, this enriched material can be further purified by any of several means including, for example, distillation, crystallization, or a second absorption step.

DETAILED DESCRIPTION OF THE INVENTION

As noted previously, the present invention is both to a shape selective adsorbant for the selective adsorption of 2,6-diisopropylnaphthalene from a feed stream of mixed diisopropylnaphthalenes as well as to a process for separating the 2,6-diisopropyl isomer from a mixture of isomers of diisopropylnaphthalenes. This can be done as a batch process while establishing a unit operation by moving the feed stream of mixed isomers over a bed of suitable adsorbant. This is conducive to commercializing the present process, for large quantities of mixed dialkylated naphthalene isomers can be processed in such a unit operation. The present process can be carried out employing, for example, chemical processing equipment used previously for such things as liquid bulk separations. For example, FIG. 1 illustrates a schematic representation of such bulk separation equipment as employed by UOP for the adsorptive separation of p-dialkylbenzene from other dialkylbenzene isomers. See D. B. Broughton, "Bulk Separations Via Adsorptions", *Chemical Engineering Progress*, pp. 49–51 (October, 1977). However, it must be emphasized that virtually any well known packed column can be employed insuring a flow of liquid feed stock and desorbant over a fixed bed of adsorbant which can be employed as a powder, pellet, or extrudate.

Referring to FIG. 1, the preferred process utilizes a column 2 filled with a fixed bed of adsorbant. The column has numerous ports 4 for feeding dialkylnaphthalene feed and desorbant as well as removing raffinate and extract. These ports are all piped to a rotary valve 8 which controls where in the adsorption column materials are fed and withdrawn. For a period of time, dialkylnaphthalene feed is provided to a section of the adsorption column wherein the adsorbant selectively adsorbs the desired 2,6-diisopropylnaphthalene isomer. The raffinate now depleted in the desired 2,6-diisopropylnaphthalene isomer is either recycled by pump 6 or withdrawn and sent to a column 10 where any desorbant it picks up is separated and returned. At a later period in time, the rotary valve 8 redirects the stream and now desorbant is fed over the portion of the packed bed which had previously adsorbed the desired 2,6-diisopropylnaphthalene isomer. The desorbant releases the desired isomer (the extract) from the adsorbant and passes through the rotary valve to a column 12 in which 2,6-diisopropylnaphthalene is separated from the desorbant.

If the 2,6-diisopropylnaphthalene enriched product does not contain sufficient purity of the desired isomer, it can be further purified by another adsorption step, fractional crystallization, or other conventional separation means.

The adsorbants employed for the preferential removal of the 2,6-diisopropyl isomer from a feed stock of mixed dialkylated naphthalenes are one or more crystalline molecular sieves such as those taught in Applicants' co-pending U.S. application Ser. No. 254,284, filed on Oct. 5, 1988, entitled SELECTIVE ISOPROPYLATION OF NAPHTHALENES TO 2,6-DIISOPROPYLNAPHTHALENES, the disclosure of which is hereby incorporated by reference. Broadly, the adsorbants of the present invention for the selective adsorption of 2,6-diisopropylnaphthalene from other diisopropylnaphthalene isomers are crystalline molecular sieves containing 12 membered oxygen rings and pore aperture dimensions between approximately 5.5Å and 7.0Å.

Shape selective adsorption occurs when the zeolite framework and its pore structure allow molecules of a given size and shape to preferentially diffuse into and adsorb within the intracrystalline free space. It is therefore important to characterize accurately the pore structure that is encountered in the various crystalline molecular sieve frameworks. Pore structure (dimensions and network) varies greatly among zeolites. Without modifications of the zeolite structure, the lowest pore aperture dimension is about 2.6Å and the highest is 7.4Å. Maximum values for the four-, six-, eight-, ten-, and twelve-membered oxygen rings have been calculated to be 2.6 Å, 3.6 Å, 4.2 Å, 6.3 Å, and 7.4 Å, respectively. Pores may lead to linear, parallel, or interconnected channels or may give access to larger intracrystalline cavities, sometimes referred to as cages. For all zeolites, the pore opening is determined by the free aperture of the oxygen ring that limits the pore aperture.

The free diameter values given in the channel description and on the ring drawings (not shown here) are based upon the atomic coordinates of the type species in the hydrated state and an oxygen radius of 1.35 Å, as determined from x-ray crystallographic data. Both minimum and maximum values are given for noncircular apertures. In some instances, the corresponding interatomic distance vectors are only approximately coplanar; in other cases the plane of the ring is not normal to the direction of the channel. Close inspection of the framework and ring drawings should provide qualitative evidence of these factors. Some ring openings are defined by a very complex arrangement of oxygen atoms. Included are references to publications which contain extensive drawings and characterization data. The relevant portions of those references are incorporated herein. It should be noted that crystallographic free diameters may depend upon the hydration state of the zeolite particularly for the more flexible frameworks. It should also be borne in mind that effective free diameters can be temperature dependent.

As used throughout the instant specification, the term "pore aperture" is intended to refer to both the pore mouth at the external surface of the crystalline structure, and to the intracrystalline channel, exclusive of cages. When a crystalline molecular sieve is hereinafter characterized by a "pore aperture dimension," adopted is the geometric dimensional analysis defined as þcrystallographic free diameter of channels" in Meier, W. M., Olson, D. H., *Atlas of Zeolite Structure Types*, (Butterworth's, 1987, 2d Rev. Ed.). The term "dimension" is preferred over "diameter" because the latter term implies a circular opening, which is not always accurate in crystalline molecular sieves.

Crystalline molecular sieves which are useful in practicing the present process include MeAPSO-46, offretite, ZSM-12 and synthetic mordenite. Preferred adsorbants are synthetic mordenite, with pore aperture dimensions of 6.5 Å and 7.0 Å and ZSM-12 with pore aperture dimensions of 6.2 Å, 5.7 Å and 5.5 Å. These preferred adsorbants can be used in the adsorption process without any pretreatment to modify their pore aperture dimensions. Synthetic mordenite is particularly preferred while other useful adsorbents may be obtained by treatment of an acidic crystalline molecular sieve having pore aperture dimensions greater than 7.0 Å selected from the group consisting of zeolite L, zeolite Beta, faujasite and SAPO-5 to reduce the dimensions of the pore apertures. Mordenite, ZSM-12, offretite and MeASPO-46 fall into the first class of adsorbants whose pore aperture dimensions are between 5.5 Å and 7.0 Å, prior to any modification to their pores.

The preferred adsorbants, mordenite and ZSM-12, as well as other suitable sieves, can be optimized to greater selective adsorption of the desired 2,6-diisopropylnaphthalene without substantially altering their pore dimensions by modifying the hydrophobic character of the molecular sieves. One such modification to the preferred adsorbants is to dealuminate. Dealumination of acidic crystalline molecular sieve materials can be achieved by exposing the molecular sieve to mineral acids such as HCl. The desired degree of dealumination will dictate the strength of acid used and the time during which the crystalline structure is exposed to the acid. It is also common to use a steam treatment in combination with the acid leach to dealuminate the zeolite materials. For additional methods of preparing aluminum-deficient zeolites, see J. Scherzer, "The Preparation and Characterization of Aluminum-Deficient Zeolites", Thaddeus E. Whyte et al., "Catalytic Materials: Relationship Between Structure and Reactivity", ACS Symposium Series 248, pp. 156–60 (American Chemical Society, 1984). Dealumination according to the instant invention is intended to achieve a Si:Al ratio above 3 and preferably above 15. Dealumination can also be applied to the second class of molecular sieve materials whose pore aperture dimensions exceed 7.0 Å.

A dealuminated crystalline molecular sieve can be calcined at temperatures between 400° C. and 1000° C., preferably between 400° C. and 600° C. Calcination serves to dehydrate or "heal" Si-OH bonds or "nests" after dealumination. Healing these nests provides for a more uniform pore structure within the crystalline material, leading to structural stability and ultimately resulting in improved adsorption. For a zeolite like hydrogen mordenite, the optimal temperature range was found experimentally to lie between 400° C. and 600° C., but preferentially at 500° C. See Mathur, Kuldeep, Narain, Ph.D. Thesis, University of Pittsburgh, 1977. In the case of H-mordenite, removal of extra and intra crystalline water can be accomplished effectively in the presence of an atmosphere of oxygen or nitrogen.

As previously noted, other adsorbants may also be considered which have aperture dimensions in excess of 7.0 Å. These other adsorbants are obtained by a combination of modifications of commercially available, acidic crystalline molecular sieve products. Examples of such sieves include zeolite L, zeolite Beta, faujasite and SAPO-5, which have 12 membered oxygen rings whose pore aperture dimensions typically exceed 7.0 Å. SAPO is an acronym for silicoaluminophosphate molecular sieves, first reported in 1984. See U.S. Pat. No. 4,440,871 to B. M. Lok et al. MeAPO is an acronym for metalaluminophosphate molecular sieves reported in U.S. Pat. No. 4,567,029 to S. T. Wilson et al. For more complete characterizations of each of the catalyst members discussed above, see Flanigen, E. M., et al., *Stud. Surf. Sci. Cat.*, 28, pp. 103-12. Also, see E. G. Derouane, "Diffusion and Shape-Selective Catalysis in Zeolites", *Intercalation Chemistry*, pp. 112-14, Ed. by M. Stanley Whittingham (Academy Press, 1982). Also, see S. Ernst, *Zeolites*, Vol. VII, p. 458 (1987), for a good discussion of ZSM-12.

When using adsorbants obtained by the treatment of crystalline molecular sieves whose pore aperture dimensions are initially above 7.0 Å, internal acid site modification can be used to reduce the pore aperture dimensions to an extent which show an enhanced 2,6-diisopropylnaphthalene selectivity. Molecular sieves with reduced port aperture dimensions are best described with reference to their performance in the adsorption under consideration. Those crystalline molecular sieves which have been adequately modified by internal acid site treatment will perform the selective adsorption of 2,6-diisopropylnaphthalene.

Ion exchange can be used to treat crystalline molecular sieves whose pore aperture dimensions are initially above 7.0 Å and reduce the pore aperture to the desired range. Elements suitable for ion exchange include alkali metals and alkali earth metals.

Crystalline molecular sieves may be treated to modify internal acid sites by contact with reagents selected from the group consisting of halogen, hydridic and organic derivatives of group 3A, 4A, 4B and 5A. Preferred embodiments of the internal acid site reagents include $B_2H_6$, $SiH_4$ and $PH_3$. For a more complete discussion of the internal acid site modification techniques contemplated herein, see A. Thijs et al., *J. Chem. Soc. Faraday Trans.*, 79, 2821 (1983). See also J. Philippaerts et al., "The Implantation of Boron-Nitrogen Compounds in Mordenite LP and Their Influence on the Adsorption Properties", *Stud. Surf. Sci. Catal.*, 28, pp. 305-10 (1986). The relevant portions of each of these citations are incorporated herein by reference.

In addition to the use of the above-described reagents which tend to be nonspecific, there is an intermediate level of crystalline molecular sieve modification which can be used to perform "pore mouth engineering". These reagents provide an intermediate level since they are not specific for external acid site, but are not entirely nonspecific, leading to substantial internal acid site modification. In selecting an intermediate reagent, the characteristics and pore aperture dimensions of the starting crystalline molecular sieve must be matched against the molecular dimensions of the reagent.

It has been shown that chemical vapor deposition of $Si(OCH_3)_4$ on H-mordenite can be successfully used to control the intracrystalline pore aperture without substantially affecting the adsorbant's internal surface acid properties. $Si(OCH_3)_4$ can be deposited irreversibly on zeolite without entering the intracrystalline pores. See Niwa, M. et al., *J. Chem. Soc., Faraday Trans.*. 1, 1984, 80, pp. 3135-45; Niwa, M. et al., "Modification of H-Mordenite by Vapor-Phase Deposition Method", *J. Chem. Soc. Commun.*, p. 819-20 (1982).

Similarly, chemical vapor deposition of metal chlorides such as $SiCl_4$, $GeCl_4$, $TiCl_4$, and $SnCl_4$ can be effective to modify pore mouth structures. These metal molecules with a range of molecular dimensions can be selected to be larger than the adsorbant pore aperture, thereby preventing substantial diffusion into the internal pore. See Hidalgo, T. V. et al., *Zeolites*, 4, pp. 175-80 (April, 1984).

The pore-modifying agents can be contacted with the molecular sieves in either solution or in vapor phase.

As noted previously, the crystalline molecular sieve adsorbant can be supplied as a powder, pellet or extrudate. Pellets and extrudates can be made according to known techniques for binding power. Pellets can be formed by applying pressure to powder. Pellets and extrudates can be formed by using binders such as alumina, clays, silica, or can be silica-alumina as well known in the art. In one embodiment of the process, the adsorbant is packed in a column and a stream of mixed diisopropylnaphthenes pass through the column. After a suitable contact time with the adsorbant bed, the depleted dialkylnaphthalene stream is purged from the packed bed. In a second step, a desorbant is fed to the column to remove the adsorbed isomers. The stream containing the desorbant and the adsorbed isomers is collected. The dialkylate fraction of this stream which is enriched in 2,6-diisopropylnaphthalene, can be separated from the desorbant by any conventional separation means such as by crystallization, thermal distillation or chromatographic adsorption. It is also contemplated that a series of adsorption/desorption cycles can be employed.

The desorbant is a liquid chosen to selectively desorb the isomers absorbed by the adsorbant. The desorbant is also chosen as a material which is easily and efficiently separated from the desired 2,6-diisopropyl isomer. In this regard, it was found that various alcohols, ethers, single ring alkylaromatics such as p-xylene and o-xylene are particularly preferred while other desorbants contemplated for use herein include m-xylene, toluene, ethylbenzene, n-propylbenzene, isopropylbenzene, 4-ethyltoluene, 1,2,4-trimethylbenzene, p-diethylbenzene, p-cymene, 1,2,3,4-tetrahydronaphthalene and mixtures thereof.

The temperature and pressure conditions for the adsorption process also affect the diffusion rate. The temperature must be between ambient and 300° C., preferably between 100° C. and 200° C. The pressure in the packed column must be between 0 psia and 5000 psia, preferably about atmospheric pressure but in any case higher than the vapor pressure of the alkylnaphthalene feed at the temperature of the adsorption step.

EXAMPLE 1

A ¼ inch O. D. stainless steel tube 12 inches long was packed with a steam de-aluminated, acid washed and calcined mordenite powder (381-10, Si/Al=23). The column was heated to a temperature of 104°-119° C. and a sample of a dialkylnaphthalene stream was pumped over the bed at a rate of 0.25 ml/min. Analysis of the initial liquid exiting the column showed a depletion of 2,6-diisopropylnaphthalene isomer over that contained in the feed stream (Table 1).

TABLE 1

| Total Isomer/DIPN's | Initial Ratio (% by Wt.) | Final Ratio (% by Wt.) |
| --- | --- | --- |
| 2,6 | 18.8 | 4.9 |
| 2,7 | 15.8 | 10.7 |
| 1,3 | 20.6 | 30.1 |
| 1,5 | 4.0 | 3.8 |
| 1,4 | 8.1 | 11.3 |
| 1,6 | 17.0 | 24.3 |
| 1,7 | 14.2 | 12.8 |
| TOTAL | 98.5 | 97.9 |
| 2,6/2,7-DIPN | 1.2 | 0.5 |

These data show that the 2,6-diisopropylnaphthalene isomer was preferentially removed from the dialkylnaphthalene stream since the 2,6/2,7 ratio dropped from 1.2 to 0.5. Also the percentage of the 2,6-diisopropyl isomer changed from 18.8 to 4.9% further illustrating the selection of this isomer by the adsorbant.

EXAMPLE 2

The mordenite sieve used in Example 1 was loaded into a ¼ inch diameter stainless steel tube 12 inches long. A mixture of diisopropylnaphthalene was pumped over ca. 1.8 gm of the sieve at 157° C. at 0.25 ml/min. Samples of the dialkylnaphthalenes passing over the mordenite bed were collected at 0.5 ml increments. Table 2 shows the mole % composition of the dialkylnaphthalene stream fed to the column. The initial 2,6/2,7 ratio was 1.19. Table 3 shows the 2,6/2,7 ratio for the samples collected after contact with the mordenite. The data shows that the 2,6/2,7 ratio dropped from 1.19 to 0.5 after 4.3 were pumped.

TABLE 2

| Mole % Composition of DIPN | |
| --- | --- |
| Isomer | mol % |
| 2,6 | 18.8 |
| 2,7 | 15.8 |
| 1,3 | 20.6 |
| 1,5 | 4.0 |
| 1,4 | 8.1 |
| 1,6 | 17.0 |
| 1,7 | 14.2 |

TABLE 3

| 2,6/2,7 Ratio of Adsorbed DIPN | |
| --- | --- |
| volume pumped (ml) | 2,6/2,7 |
| 4.3 | 0.50 |
| 5.0 | 1.13 |
| 7.0 | 1.17 |
| 9.5 | 1.19 |

After pumping 9.5 ml of dialkylnaphthalene, the 2,6/2,7 ratio finally reached the initial value. After the 2,6/2,7 ratio was at the initial value of 1.19 the dialkylnaphthalene feed stream was turned off and p-xylene was pumped to flush the adsorbed 2,6-diisopropylnaphthalene from the sieve. FIG. 2 shows the ratio of the 2,6-diisopropyl isomer/total dialkylated naphthalenes as a function of the amount of xylene pumped. From the graph it can be seen that the first material eluted is probably the original dialkylate displaced from the void space between the mordenite particles, since the 2,6/total isomers is 0.2 (or 20%) initially. The maximum in the curve is due to the 2,6-isomer being displaced from the pore of the sieve. The enrichment is significant since the sample taken at 6.8 ml contains 54% 2,6-DIPN as compared to 19% in the initial dialkylate mixture.

What is claimed is:

1. A process for enriching the fraction of 2,6-diisopropylnaphthalene contained in a feed stream of mixed diisopropylnaphthalenes comprising contacting said feed stream with an adsorbant bed containing one or more crystalline molecular sieves being characterized as having twelve membered oxygen rings and pore aperture dimensions between approximately 5.5 Å and 7.0 Å and which demonstrate shape selective preference for 2,6-diisopropylnaphthalene over other dialkylated naphthalenes, separating said feed stream from said adsorbant bed and contacting the adsorbant bed with a desorbant capable of substantially desorbing said 2,6-diisopropylnaphthalene from the pores of said crystalline molecular sieves.

2. The process of claim 1 wherein the temperature of said feed stream contacting said adsorbant bed is maintained between approximately ambient and 300° C.

3. The process of claim 1 wherein the temperature of said feed stream contacting said adsorbant bed is maintained between approximately 100° C. and 200° C.

4. The process of claim 1 wherein the pressure maintained within said adsorbant bed is between approximately 0 to 5000 psi.

5. The process of claim 1 wherein the pressure maintained within said adsorbant bed is approximately 15 psia.

6. The process of claim 1 wherein said one or more crystalline molecular sieves are members selected from the group consisting of ZSM-12, offretite, MeAPSO-46 and mordenite.

7. The process of claim 1 wherein said one or more crystalline molecular sieves are characterized as possessing a silicon to aluminum ratio greater than 3.

8. The process of claim 1 wherein said one or more crystalline molecular sieves are characterized as possessing a silicon to aluminum ratio greater than 15.

9. The process of claim 1 wherein said desorbant is characterized as having a molecular size and dimension equal to or less than that of 2,6-diisopropylnaphthalene.

10. The process of claim 7 wherein said desorbant comprises one or more members selected from the group consisting of alcohols, ethers, single ring alkylaromatics such as p-xylene, o-xylene, m-xylene, toluene, ethylbenzene, and propylbenzene, isopropylbenzene, 4-ethyltoluene, 1,2,4-trimethylbenzene, p-ethyltoluene, 1,2,4-trimethylbenzene, p-diethylbenzene, p-cymene, and 1,2,3,4-tetrahydranaphthalene and mixtures thereof.

11. The process of claim 1 further comprising the step of passing said desorbant and those components from the fed stream contained in said desorbant bed through said adsorbant bed or another adsorbent bed to further enrich the fraction of 2,6-diisopropylnaphthalene.

12. The process of claim 1 further comprising the step of substantially separating said desorbant from those components contained in the desorbant as a result of contacting said desorbant with said adsorbant bed.

13. The process of claim 12 wherein said separation is carried out by fractional crystallization.

14. The process of claim 7 wherein said adsorbant is calcined at a temperature between approximately 400° C. and 600° C.

15. The process of claim 8 wherein said one or more crystalline molecular sieves are subjected to dealumination to achieve an Si:Al ratio greater than 15.

16. A process for separating the isomer 2,6-diisopropylnaphthalene from a quantity of mixed isomers of dialkylated naphthalenes comprising contacting said quantity of mixed isomers with an adsorbent bed containing one or more crystalline molecular sieves being characterized as having twelve membered oxygen rings and pore aperture dimensions between approximately 5.5 Å and 7.0 Å and which demonstrate shape selective preference for the 2,6-diisopropylnaphthalene isomer over other dialkylated naphthalene isomers, separating the adsorbant bed from the mixed isomers, followed by contacting the adsorbant bed with a desorbant for desorbing the 2,6-diisopropylnaphthalene isomer from the pores of the crystalline molecular sieves.

17. The process of claim 16 wherein the temperature of said feed stream contacting said adsorbant bed is maintained between approximately ambient and 300° C.

18. The process of claim 16 wherein the temperature of said feed stream contacting said adsorbant bed is maintained between approximately 100° C. and 200° C.

19. The process of claim 16 wherein the pressure maintained within adsorbant bed is between approximately 0 to 5000 psia.

20. The process of claim 16 wherein the pressure maintained within said adsorbant bed is approximately 15 psia.

21. The process of claim 16 wherein said one or more crystalline molecular sieves are member selected from the group consisting of ZSM-12, offretite, MeAPSO-46 and mordenite.

22. The process of claim 19 wherein said one or more crystalline molecular sieves are characterized as possessing a silicon to aluminum ratio greater than 3.

23. The process of claim 16 wherein said desorbant is characterized as having a molecular size and dimension equal to or less than that of 2,6-diisopropylnaphthalene.

24. The process of claim 19 wherein said desorbant comprises a member selected from the group consisting of alcohols, ethers, single ring alkylaromatics such as p-xylene, o-xylene, m-xylene, toluene, ethylbenzene, and propylbenzene, isopropylbenzene, 4-ethyltoluene, 1,2,4-trimethylbenzene, p-diethylbenzene, p-cymene, and 1,2,3,4-tetrahydranaphthalene and mixtures thereof.

25. The process of claim 16 wherein said desorbant is substantially separated from those components contained in the desorbant as a result of contacting said desorbant with said adsorbant bed.

26. The process of claim 25 where separating the desorbant from those components contained in the desorbant by contacting said desorbant with the adsorbent bed is carried out by fractional crystallization.

27. The process of claim 16 wherein said adsorbant is calcined at a temperature between approximately 400° C. and 600° C.

28. The process of claim 16 wherein said one or more crystalline molecular sieves are characterized as processing a silicon to aluminum ratio greater than 15.

29. The process of claim 28 wherein said one or more crystalline molecular sieves are subjected to dealumination to achieve an Si:Al ratio greater than 15.

30. The process of claim 6 where the one or more molecular sieves is mordenite.

31. The process of claim 21 where the one or more molecular sieves is mordenite.

* * * * *